(12) United States Patent
Carr

(10) Patent No.: US 7,197,356 B2
(45) Date of Patent: Mar. 27, 2007

(54) MICROWAVE DETECTION APPARATUS

(75) Inventor: Kenneth L. Carr, Woolwich, ME (US)

(73) Assignee: Meridian Medical Systems, LLC, Ayer, MA (US)

( * ) Notice: Subject to any disclaimer, the term of this patent is extended or adjusted under 35 U.S.C. 154(b) by 507 days.

(21) Appl. No.: 10/847,975

(22) Filed: May 18, 2004

(65) Prior Publication Data

US 2004/0249272 A1 Dec. 9, 2004

Related U.S. Application Data

(63) Continuation-in-part of application No. 10/452,154, filed on Jun. 2, 2003, now Pat. No. 6,932,776.

(51) Int. Cl.
*A61B 5/00* (2006.01)

(52) U.S. Cl. .................. 600/430; 600/549; 374/122

(58) Field of Classification Search ................ 600/430, 600/549; 374/122; 607/100–102
See application file for complete search history.

(56) References Cited

U.S. PATENT DOCUMENTS

| 4,557,272 | A |   | 12/1985 | Carr |
| 4,583,556 | A |   | 4/1986  | Hines et al. |
| 5,057,106 | A |   | 10/1991 | Kasevich et al. |
| 5,344,435 | A | * | 9/1994  | Turner et al. ............ 607/101 |
| 5,904,709 | A |   | 5/1999  | Arndt et al. |
| 5,949,845 | A | * | 9/1999  | Sterzer .................... 378/37 |
| 6,047,216 | A |   | 4/2000  | Carl et al. |
| 6,210,367 | B1 |  | 4/2001  | Carr |
| 6,408,204 | B1 |  | 6/2002  | Hirschman |
| 6,475,159 | B1 |  | 11/2002 | Casscells et al. |
| 6,496,736 | B1 |  | 12/2002 | Carl et al. |
| 6,496,738 | B2 |  | 12/2002 | Carr |
| 6,860,851 | B2 |  | 3/2005  | Knudson et al. |
| 2002/0103445 | A1 | | 8/2002 | Rahdert et al. |
| 2002/0111560 | A1 | | 8/2002 | Kokate et al. |

OTHER PUBLICATIONS

Diller, Wendy "The Coming of Age of Vulnerable Plaque", Windhover Information Inc. Start-up, Nov. 2000. pp. 1-10.

* cited by examiner

*Primary Examiner*—Ruth S. Smith
(74) *Attorney, Agent, or Firm*—John F. McKenna; Cesari & McKenna, LLP

(57) ABSTRACT

Microwave detection apparatus includes an intravascular catheter containing inner and outer conductors, the distal ends of the conductors forming an antenna at a distal end of the catheter. A gap is provided in the inner conductor near the antenna thereby forming spaced-apart opposing proximal and distal inner conductor segments between which is connected an electrical circuit. That circuit includes a temperature reference and a Dicke-switch switchable in response to a switching signal between a first condition wherein the switch connects the proximal inner conductor segment to the temperature reference thereby delivering a temperature reference signal from the temperature reference to the proximal ends of the conductors and a second condition wherein the switch connects the proximal inner conductor segment to the distal inner conductor segment thereby delivering an antenna signal from the antenna to the proximal ends of the conductors.

11 Claims, 2 Drawing Sheets

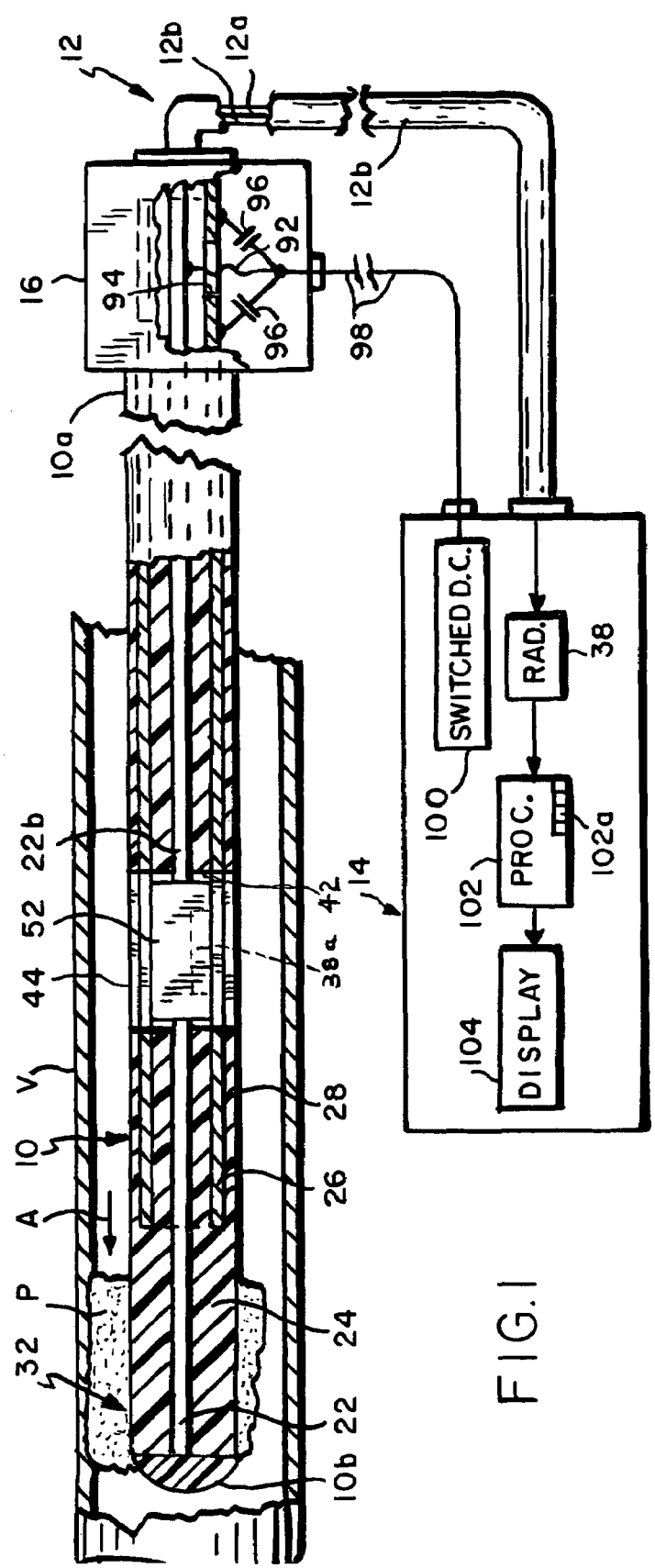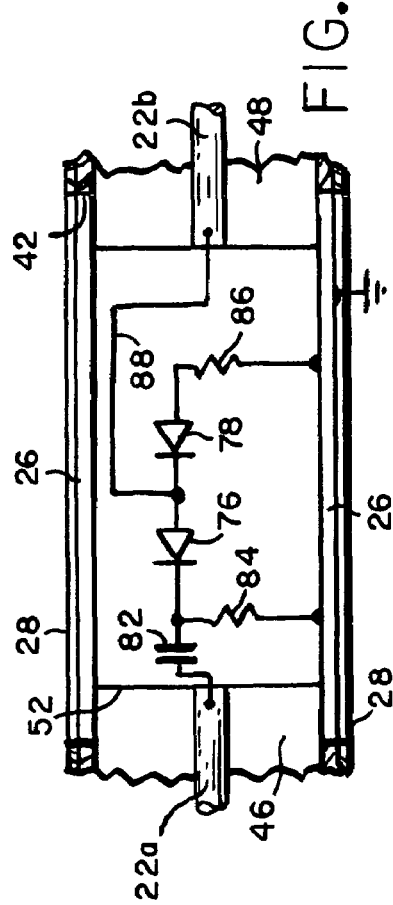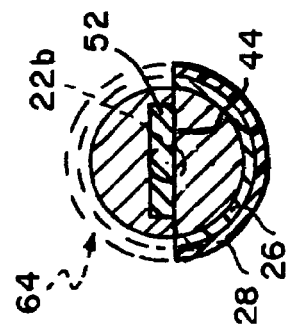

MICROWAVE DETECTION APPARATUS

CROSS-REFERENCE TO RELATED APPLICATION

This application is a continuation-in-part of Ser. No. 10/452,154, filed Jun. 2, 2003, now U.S. Pat. No. 6,932,776, the contents of which are hereby incorporated by reference herein.

This invention relates to microwave detection apparatus. It relates especially to apparatus for detecting vulnerable plaques utilizing microwave radiometry.

BACKGROUND OF THE INVENTION

1. Field of the Invention

It is widely known that many heart attacks originate from blockages created by athrosclerosis which is the aggressive accumulation of plaques in the coronary arteries. The accumulation of lipids in the artery and resulting tissue reaction cause a narrowing of the affected artery which can result in angina, coronary occlusion and even cardiac death.

Relatively recent studies have shown that coronary disease can also be caused by so-called vulnerable plaques which, unlike occlusive plaques, are engrained or imbedded in the arterial wall and do not grow into the blood vessel. Rather, they tend to erode creating a raw tissue surface that forms caps or scabs. Thus, they are more dangerous than occluding plaque which usually give a warning to a patient in the form of pain or shortness of breath. See, e.g., The Coming of Age of Vulnerable Plaque, Diller, W., Windover's Review of Emerging Medical Ventures, November 2000.

2. Description of the Prior Art

Since vulnerable plaques are contained within the vessel wall, they may not result in a closing or narrowing of that vessel. As a result, such plaques are not easily detectable using conventional x-ray, ultrasound and MRI imaging techniques.

Moreover, since vulnerable plaques are part of the vessel wall, they may have essentially the same temperature as the surrounding normal tissue and the blood flowing through the vessel. Therefore, they are not amenable to detection by known intravascular catheters which rely on infrared (IR) imaging, thermisters, thermocouples and the like in order to detect temperature differences in the vessel wall.

Such intravascular heat sensing catheters are disadvantaged also because they usually incorporate an inflatable balloon to isolate the working each end of the catheter from fluids in the vessel; see for example U.S. Pat. No. 6,475,159. As seen there, the IR detector is located within the balloon which constitutes an insulating (not transparent at IR frequencies) layer between the detector and the vessel wall causing significant attenuation of the signal from the detector. Also, the undesirable stoppage of blood flow by the balloon increases the risk to the patient. Still further, the balloon has to be repeatedly inflated and deflated in order to image different locations along the blood vessel increasing the operating time during which the patient is at risk.

In my above-identified patent application, an intravascular catheter is described which contains a microwave antenna and is able to pick up the presence of vulnerable plaques engrained in the wall of a suspect blood vessel as it is moved along that vessel. The antenna, in combination with an external microwave detection and display unit, detects and displays thermal anomalies due to the difference in the thermal emissivity (brightness) of vulnerable plaques as compared to normal tissue even though the two may have a common temperature. In other words, it has been found that the microwave characteristics of vulnerable plaques imbedded in a vessel wall are different from those of normal tissue comprising the vessel wall and this difference is detected as a thermal anomaly and displayed or plotted as the catheter is moved along the vessel.

In my prior application, the microwave antenna is located at the distal or working end of the catheter. The inner and outer conductors of the antenna are connected by a coaxial cable to the external detection and display unit which includes a radiometer that detects the microwave emissions from the blood vessel picked up by the antenna. The radiometer produces corresponding output signals for a display which responds to those signals by displaying the thermal emissions from the blood vessel in real time as the catheter is moved along the vessel.

The radiometer is preferably a Dicke-type radiometer and a temperature reference, reflecting the temperature of the blood flowing through the vessel which corresponds to the body's core temperature, is used as the radiometer reference. The operating frequency of the radiometer is selected to detect microwave emissions from a depth in the blood vessel wall where vulnerable plaques are likely to be imbedded. Thus as the catheter is moved along the vessel, it is maintained at a constant background or core temperature corresponding to the temperature of the blood and of normal tissue. The locations of vulnerable plaques are detected as thermal anomalies (hot spots) due to the higher emissivity of the plaques as compared to normal tissue. Using the output of the radiometer to control a display, the plaque sites along the vessel can be plotted.

While the apparatus embodiments disclosed in the above parent application are satisfactory in many respects, they have certain drawbacks. More particularly, the Dicke-type radiometer is a comparison radiometer system. Therefore, it requires a Dicke switch to alternately connect the antenna (the unknown temperature to be detected) and the reference temperature, e.g. a stable noise source or temperature sensor.

Every component of such a radiometer generates noise power that contributes to the overall noise of the system. Therefore the total apparatus output contains not only noise received by the antenna, but also noise generated within the apparatus itself. Such variations within the apparatus can produce output fluctuations far greater than the signal level to be measured. To overcome these gain variations, Dicke developed the common load comparison radiometer. This configuration greatly reduces the effects of short-term gain fluctuations in the radiometer since the switch provides a mechanism to allow both the reference and the unknown signals to pass through the apparatus essentially at the same time relative to expected gain drift in the radiometer's amplifiers such that any drifting gain will be applied equally to both the antenna and the reference signals.

Since radiometer receiver input is switched at a constant rate by the Dicke switch between the antenna and the constant-temperature reference load, the switched or modulated RF signal should, therefore, be inserted at a point prior to RF amplification in the radiometer and as close to the antenna as possible. Any component or transmission line located between the unknown temperature being detected and the Dicke switch can introduce an error, i.e. due to changes in environment, motion, etc.

In the apparatus disclosed in my above-identified application, a temperature reference in the form of a resistive load may be provided at the distal end of the catheter to provide a signal corresponding to the patient's core temperature. That approach, however, requires an antenna with a cablewithin-a-cable or tri-axial configuration as well as a quarter-wave stub diplexer, to deliver these signals to the radiometer which is located in the external detection and display unit. The inner conductor of the coaxial cable, although in the same environment and subject to the same flexing, is smaller in diameter and therefore not identical to the cable's outer conductor(s). This produces a difference in the gain of the antenna signal verses the reference signal and thus introduces an error into the output of the apparatus as a whole.

Also as noted above, the antennas described in my parent application require a quarter-wave stub diplexer to couple the antenna and reference signals to the external radiometer. This complicates, and increases the cost of, the apparatus disclosed there.

While we will describe the subject apparatus in the context of plaque detection, it should be understood that it may also be use in other applications such as tumor detection, non-invasive temperature monitoring, etc.

SUMMARY OF THE INVENTION

Accordingly, it is an object of the present invention to provide improved microwave detection apparatus for detecting temperature variations in a human or animal body.

Another object of the invention is to provide such apparatus capable of detecting vulnerable plaques.

Yet another object of the invention is to provide apparatus of this type which is relatively easy and inexpensive to make.

A further object of the invention is to provide such apparatus which produces a temperature-indicating output signal having a minimum amount of noise.

Other objects will, in part, be obvious and will, in part, appear hereinafter.

The invention accordingly comprises the features of construction, combination of elements and arrangement of parts which will be exemplified in the construction hereinafter set forth, and the scope of the invention will be indicated in the claims.

Briefly, the present apparatus is similar to the ones described in my above parent application in that it includes a catheter for insertion into a patient, the catheter being connected by cabling to an external detection and display unit containing a Dicke-type radiometer. It differs, however, in that at least the Dicke switch component of the radiometer is integrated right into the catheter along with the temperature reference so that the antenna signal and the reference signal have essentially the same gain and can be conducted from the catheter's antenna to the radiometer on a single coaxial cable and without requiring a quarter-wave diplexer. Therefore, the apparatus has a higher signal-to-noise ratio than my prior comparable apparatus and is simpler and less expensive to make.

BRIEF DESCRIPTION OF THE DRAWINGS

For a fuller understanding of the nature and objects of the invention, reference should be made to the following detailed description taken in connection with the accompanying drawings, in which:

FIG. 1 is a diagrammatic view of apparatus for detecting vulnerable plaques incorporating the invention;

FIG. 1A is a sectional view, on a larger scale, taken along line 1A—1A of FIG. 1;

FIG. 3 is a fragmentary sectional view on a still larger scale showing the Dicke switch component of FIG. 1 apparatus in greater detail.

DETAILED DESCRIPTION OF AN ILLUSTRATIVE EMBODIMENT

Figure 2:
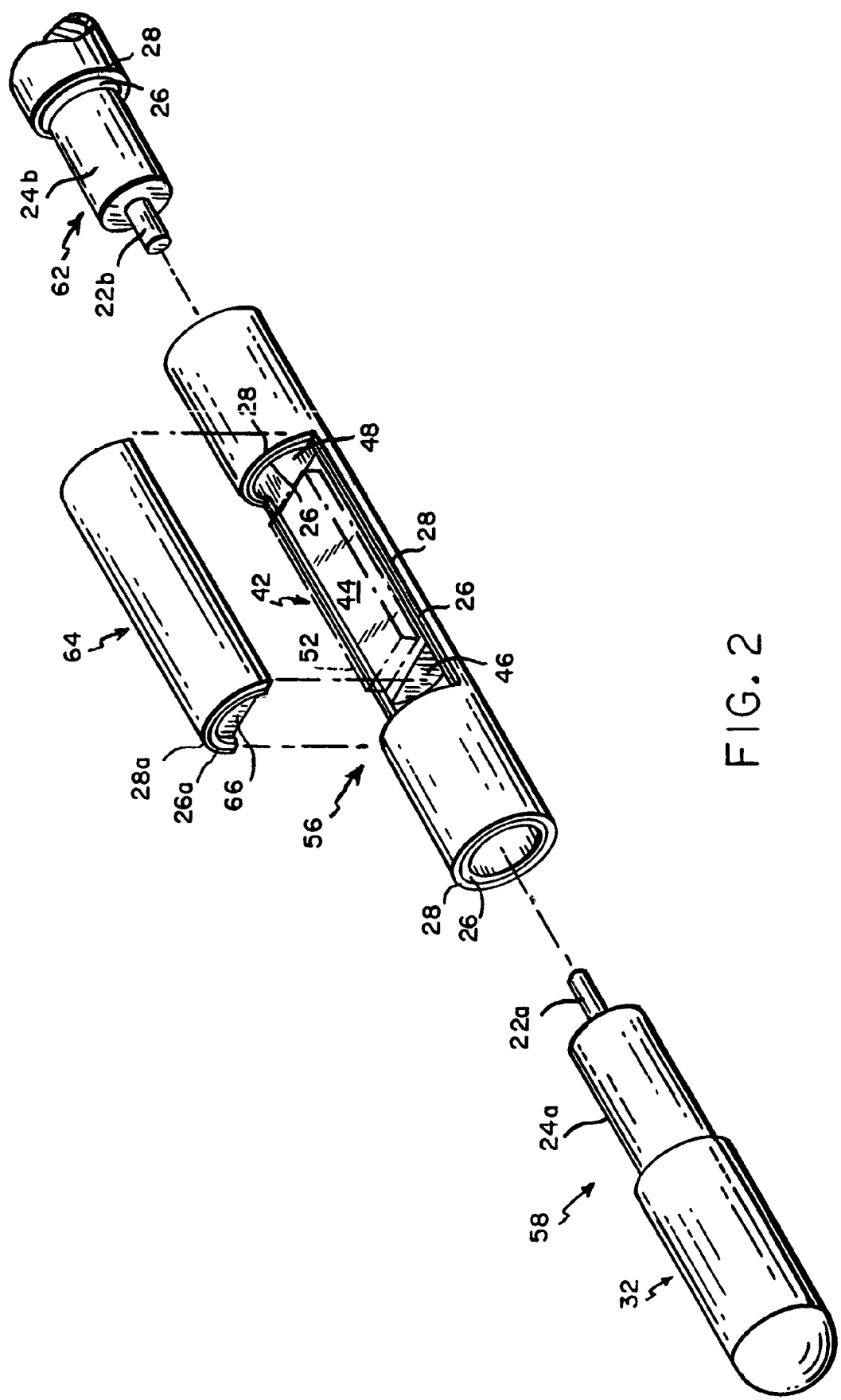
FIG. 2 is an exploded perspective view showing the catheter component of the FIG. 1 apparatus in greater detail.

Referring to FIG. 1 of the drawings, the present apparatus comprises a catheter shown generally at 10 for insertion into a blood vessel V which may have locations where vulnerable plaques P are embedded or engrained in the vessel wall. Catheter 10 is connected via a coaxial cable 12 to a detection and display unit 14. The catheter has a proximal end 10*a* to which cable 12 is connected by way of a fitting or connector 16, and a distal end or tip 10*b*. The catheter may have a length of 100 cm or more and is quite narrow and flexible so that it can be threaded along a conventional introducer, e.g. 8.5 French, allowing the distal end 10*b* of the catheter to be placed at a selected position in a patient's blood vessel V. Typically, that vessel is accessed by a vein in the patient's neck or groin.

As shown in FIG. 1, catheter 10 is basically a coaxial cable. It comprises a central conductor 22 surrounded by a cylindrical layer 24 of a suitable dielectric material, e.g. PTFE. Surrounding layer 24 is a tubular outer conductor 26. At fitting 16, the proximal ends of conductors 22 and 26 are connected to the inner 12*a* and outer 12*b* conductors of cable 12. Preferably, the catheter has a thin protective outer coating 28 of a suitable dielectric material, e.g. PTFE.

At the distal end segment of catheter 10, the inner conductor 22 extends beyond the outer conductor 26 to form a microwave antenna shown generally at 32 which, in this case, is a monopole; in some applications, a helical antenna or capacitive tip may be used. Typically, the inner conductor 22 extends beyond the outer conductor 26 a distance in the order of 1 cm so that antenna 32 has a relatively long antenna pattern.

As with the apparatus disclosed in my above-identified application, antenna 32 in catheter 10 detects the thermal radiation emitted from blood vessel V and applies a corresponding electrical signal via cable 12 to a Dicke-type radiometer 38 in unit 14. In this case, however, the Dicke switch component of that radiometer is incorporated right into catheter 10 close to the antenna 32 therein. In order to do this, as shown in FIGS. 1B and 2, a relatively long semi-cylindrical notch 42 is provided in catheter 10 behind antenna 32. More particularly, the inner conductor 22 and layer 24 thereon are interrupted and the top halves of outer conductor 26 and coating 28 thereon are removed to expose a flat, electrically conductive pad 44 which fills within the remaining lower half of outer conductor 26 and forms the bottom wall of notch 42. Preferably, semi-cylindrical recesses 46 and 48 are present at opposite ends of pad 44 for reasons to be described presently. Pad 44 is arranged and adapted to support a small IC chip 52 shown in solid lines in FIGS. 1 and 1A and in phantom in FIG. 2. This chip carries a temperature reference and all the components of a Dicke switch.

In order to install chip 52, catheter 10 is preferably made in sections as shown in FIG. 2 which sections are assembled after the chip 52 is mounted on pad 44. Thus, catheter 10 has a main section 56 which contains the notch 42. That section has tubular outer ends consisting of the outer conductor 26 and the outer coating 28. Between those ends, i.e. at notch 42, the outer conductor 26 and coating 28 are semi-cylindrical as described above to expose the conductive pad 44 which may be a solder body mostly filling the lower half of conductor 26.

Catheter 10 also includes a distal end section 58 having an exposed segment 24a of layer 24 and a projecting end 22a of conductor 22 arranged and adapted to plug into the distal end of catheter section 56. Preferably, the outer conductor 26 ends at the distal end of section 56 so that when distal end section 58 is plugged into section 56, the distal end segment of section 58 forms antenna 32. When assembled thusly, the conductor end 22a is located in recess 46 of section 56.

The final section of catheter 10 is a proximal end section 62 having an exposed segment 24b of layer 24 and a projecting end 22b of conductor 22 adapted to plug into the proximal tubular end of catheter section 56 such that the conductor end 22b is located in recess 48 of section 56.

After chip 52 is anchored in place on pad 44, the catheter sections may be permanently secured together by a suitable adhesive or bonding material applied to the outer surfaces of layer segments 24a and 24b.

The conductive pad 44 is in intimate electrical contact with outer conductor 26 and constitutes a ground plane for chip 52. The chip is also connected to the inner conductor ends 22a and 22b at the opposite ends of notch 42 by wire bonding, soldering, welding or other suitable means. Once chip 52 has been installed in section 56, notch 42 may be closed by a generally semi-cylindrical cover shown generally at 64 in FIGS. 1A (in phantom) and 2.

Cover 64 includes a semi-cylindrical segment 26a of outer conductor 26 with an outer coating segment 28a thereon. Cover 64 also includes an insulating body 66 which fills segment 26a and is shaped and arranged to receive chip 52 when the cover 64 is seated in notch 42 as shown in FIG. 1A. In other words, body 66 is recessed so that when the cover 64 is properly seated, the edges of outer conductor segment 26a in the cover butt against and electrically contact the corresponding edges of the outer conductor 26 in notch 42 so that essentially a single outer conductor 26 encircles chip 52 as well as the ends 22a, 22b of inner conductor 22 that project into notch 42. Cover 64 may be secured in place by a suitable adhesive or bonding material.

Refer now to FIG. 3 which shows the components of chip 52 connected between the inner conductor ends 22a and 22b. The chip includes series-connected diodes 76 and 78. The cathode of diode 76 is connected via a matching capacitor 82 to inner conductor end 22a and, via a resistor 84, to pad 44 constituting electrical ground. The capacitor 82 is preferably a chip capacitor and constitutes a filter which blocks the RF or microwave signal on antenna 32 and passes a DC or video bias signal. The anode of diode 78 is connected to pad 44 via a load resistor 86 which constitutes the temperature reference for radiometer 38.

To have reasonably low insertion loss and some isolation, the diodes 76 and 78 should have low series resistance and low reverse bias capacitance. A standard beam-leaded PIN diode with about 3 ohms series resistance and 0.05 pF reverse biased capacitance should suffice. A triggered bias for the diodes 76, 78 is provided via a lead 88 that connects the junction of those diodes 76 and 78 to the inner conductor end 22b. Since the reference load consisting of resistor 86 is located near antenna 32, it is maintained at substantially the same temperature as the antenna so that all variables introduced by catheter 10 are common to both the antenna which measures the unknown temperature and resistor 86 which serves as the temperature reference so that any such variables will be removed by that synchronous detection arrangement. Resultantly, the apparatus provides a very stable temperature measurement devoid of gain variations that may obscure vulnerable plaque detection.

It should be noted that the chip 52 carrying the Dicke switch in catheter 10 does not exceed the diameter of antenna 32 and does not add materially to the non-flexible length of the catheter. Therefore, the integral chip 52 does not materially decrease the ability of catheter 10 to be introduced into a patient. The various leads of the switch 52 may be transmission line strips, e.g. 5 mil alumina or the like, and the components of the switch may have the following characteristics:

| | |
|---|---|
| Capacitor 82 | 1 pF |
| Diode 76 and 78 | Metalics Part No. MPN-1036-B11 |
| Resistor 84 | 1K ohms |
| Resistor 86 | 50 ohms |

The chip 52 may have a footprint as small as 0.100 inch by 0.037 inch so that the entire chip fits within the diameter of outer conductor 26 of catheter 10.

As shown in FIG. 1, the DC biases for triggering the diodes in chip 52 are brought in on the inner conductor 22 at fitting 16. More particularly, a small diameter wire 92 is connected to the inner conductor 22 and introduced through a hole 94 in the outer conductor 26. One or more capacitors 96 is connected between the bias wire 92 and the outer conductor. The capacitor(s) 96 has a low impedance at the lower microwave frequency and a high impedance at a DC or video frequency such that the microwave signal is prevented from coupling to the bias circuit, while the bias voltage is coupled only to the inner conductor 22. The bias voltage, e.g. +/−5–10 volts (+/−10ma) is provided via a conductor 98 to bias wire 92 from a switched DC source 100 in unit 14.

The switched source 100 in unit 14 provides a switched +/−bias to the diodes in chip 52 which toggles the diodes so that signals from antenna 32 and the load resistance 86 are applied alternately to radiometer 38 in unit 14 at a switching frequency of about 100 Hz. The output of the radiometer 38 is processed by a processor 102 in unit 14 which controls a display 104 in that unit.

It should be understood that the aforesaid electrical components of my detection apparatus may be discrete parts or they may be incorporated into an integrated circuit or a microwave integrated chip (MMIC). Also, other components of the Dicke radiometer besides the switch maybe implemented in chip 52. Indeed, it is contemplated that the entire Dicke radiometer be incorporated into the chip 52 in catheter 10 as shown in phantom at 38a in FIG. 1.

To use the FIG. 1 apparatus, the catheter 10 is threaded into a patient's vessel V in the usual way. After insertion, the catheter assumes essentially the same temperature as the vessel V and the blood flowing through that vessel. This temperature, which constitutes the body's core temperature, is assumed by load resistor 86 and used as the temperature reference delivered to chip 52 which toggles between the signal values from antenna 32 and the load 86. When the catheter 10 is moved along vessel V, say in the direction of arrow A in FIG. 1, antenna 32 will pick up thermal emissions from the normal tissue in the vessel wall and unit 14 will provide a core or background temperature indication which will be displayed by display 104. When the antenna 32 is moved opposite a region containing vulnerable plaques P, the apparatus will detect a thermal anomaly due to the increased emmitance (brightness) of the plaques P embedded in the vessel wall. Thus as the catheter 10 is advanced along the vessel, the unit 14 can display continuously in real time the location of plaques P as well as other useful information such as the body's core temperature, diagnostic data and the like as instructed via the processor's keyboard 102a.

It will be seen from the foregoing that by incorporating the radiometer's Dicke switch into catheter 10, the catheter requires only two conductors and no quarter-wave stub diplexer to couple catheter 10 to the radiometer 38 in the external detection and display unit 14. This simplifies the manufacture of the apparatus and reduces its cost considerably. Of course, if the radiometer 38 is incorporated into catheter 10, the only external connectors from catheter 10 are to the power supply and processor.

It will thus be seen that the objects set forth above, among those made apparent from the preceding description, are efficiently attained and, since certain changes may be made in the construction set forth without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. Microwave detection apparatus comprising
   an intravascular catheter containing an inner conductor and an outer conductor, each conductor having proximal and distal ends, the distal ends of said conductors forming an antenna at a distal end of the catheter;
   means defining a gap in the inner conductor relatively near the antenna thereby forming spaced-apart opposing distal and proximal inner conductor segments, and
   an electrical circuit in said catheter and connected electrically between said conductor segments, said circuit including
      a temperature reference, and
      a Dicke-switch switchable in response to a switching signal between a first condition wherein the switch connects the proximal inner conductor segment to the temperature reference thereby delivering a temperature reference signal from the temperature reference to the proximal ends of the conductors and a second condition wherein the switch connects the proximal inner conductor segment to the distal inner conductor segment thereby delivering an antenna signal from the antenna to the proximal ends of the conductors, and a detector responsive to the antenna signal for providing an indication of microwave emissions picked up at the antenna.

2. The apparatus defined in claim 1 and further including a switching signal source connected electrically to the switching circuit via the inner conductor for applying a switching signal to said switch to toggle the switch between said two conditions.

3. The apparatus defined in claim 2 wherein the switching signal source comprises a switched DC voltage source.

4. The apparatus defined in claim 1 wherein the temperature reference comprises a resistor.

5. The apparatus defined in claim 1 wherein said circuit is comprises an integrated circuit chip which fits entirely within said outer conductor and is electrically grounded thereto.

6. The apparatus defined in claim 5 wherein the chip includes
   first and second series-connected diodes, each diode having a cathode and an anode;
   a first conductor connecting the cathode of the first diode to the distal inner conductor segment;
   a first resistor connecting the cathode of the first diode to the outer conductor, and
   a second conductor connecting the proximal inner conductor segment to the anode of the first diode and the cathode of the second diode,
   said temperature reference being a resistance connected electrically between the anode of the second diode and the outer conductor.

7. The apparatus defined in claim 1 and further including
   a voltage source having an output providing a switched DC bias voltage, and
   a filter device connected between said output and the proximal ends of said conductors to isolate the switching signal to the switch from the antenna signal from the antenna.

8. The apparatus defined in claim 1 wherein the detector comprises
   a radiometer operating at a selected frequency and having an input, and
   connection means electrically connecting the proximal ends of said conductors to said input.

9. The apparatus defined in claim 8 and further including
   a voltage source having an output providing a switched DC bias voltage, and
   a filter device connected between said output and the proximal ends of the conductors to isolate the switching signal to the switch from the antenna signal to the radiometer.

10. The apparatus defined in claim 9 wherein the filter device comprises
    an electrical lead extending through a hole in said outer conductor and connecting said inner conductor to the output of the voltage source, and
    a capacitance connected electrically between said outer conductor and the output of the voltage source.

11. The apparatus defined in claim 8 wherein said radiometer is contained within said catheter.

* * * * *